United States Patent [19]

Asker

[11] 4,384,575
[45] May 24, 1983

[54] EAR PROTECTION PLUG AND A METHOD FOR THE PRODUCTION OF SAME

[76] Inventor: Lambert C. C. Asker, 138 E. 36, New York, N.Y. 10016

[21] Appl. No.: 268,993

[22] PCT Filed: Oct. 2, 1980

[86] PCT No.: PCT/SE80/00237
§ 371 Date: Jun. 3, 1981
§ 102(e) Date: May 26, 1981

[87] PCT Pub. No.: WO81/00960
PCT Pub. Date: Apr. 16, 1981

[30] Foreign Application Priority Data

Oct. 3, 1979 [SE] Sweden ................................. 7908174

[51] Int. Cl.³ ............................................. A61F 11/02
[52] U.S. Cl. ............................. 128/152; 220/DIG. 19
[58] Field of Search ............... 128/152, 151, 341, 342, 128/343, 344, 130; 215/355; 220/DIG. 19

[56] References Cited

U.S. PATENT DOCUMENTS

| | | | |
|---|---|---|---|
| 2,710,427 | 6/1955 | Canton | 128/152 |
| 2,803,247 | 8/1957 | Zwislocki | 128/152 |
| 3,736,929 | 6/1973 | Mills | 128/152 |
| 3,984,022 | 10/1976 | Babiol | 215/355 |
| 4,089,332 | 5/1978 | Rose | 128/152 |

FOREIGN PATENT DOCUMENTS 507500 12/1954 Italy ................................. 215/355

Primary Examiner—Henry J. Recla
Attorney, Agent, or Firm—Barnes, Kisselle, Raisch, Choate, Whittemore & Hulbert

[57] ABSTRACT

An ear protection plug of elastic material which is characterized in that it is in the form of a closed gas-filled hollow body of approximately ovoid longitudinal section, so as to have a first relatively thick end portion (3) and an opposite relatively narrow second end portion (2). Each end portion has a decreasing cross-sectional diameter in the direction towards the respective end, such that the plug has two opposite insertion ends and permits optionally inserting the ear protection plug either with the thick or with the narrow insertion end in the ear canal to fit ear canals of varying size and/or form.

A method for the production of an ear protection plug according to the invention is characterized in that one part (11) of a mould block divided in two parts (11, 12) having a plurality of cells forming moulds and separated from each other by mould walls, is immersed in liquid plastic material such that the cells of the immersed mould part (11) are filled with liquid plastic, whereupon the mould parts are assembled and the mould block is rotated about one or more axes and is subjected to suitable temperature conditions for distribution and setting of the plastic material on the inner side of the mould cells (13).

9 Claims, 5 Drawing Figures

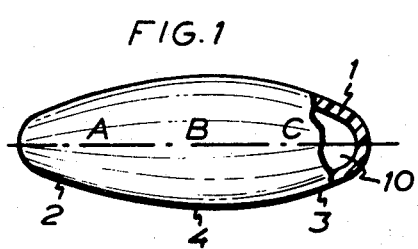
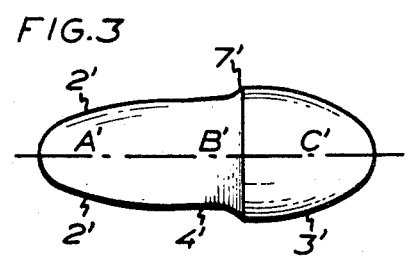
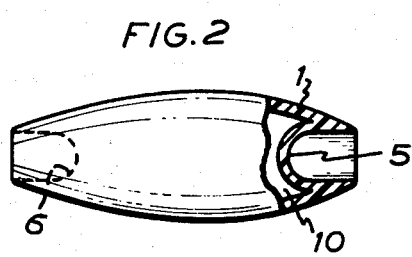
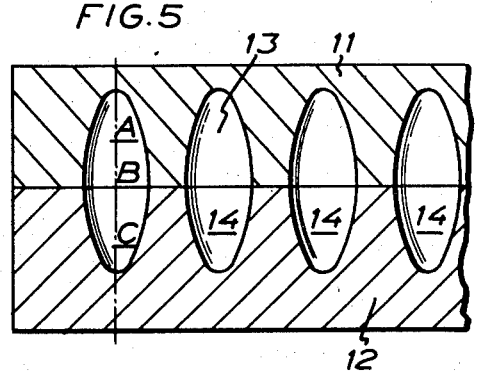
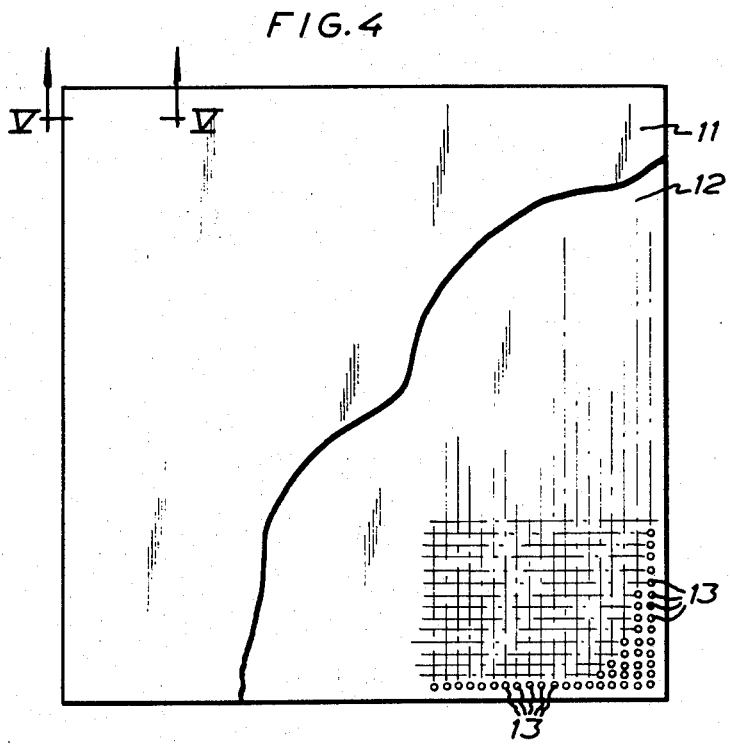

EAR PROTECTION PLUG AND A METHOD FOR THE PRODUCTION OF SAME

The present invention is directed to ear protection plugs and particularly elastically deformable ear protection plugs of the type which can be disposed of after use.

As is well known, an ear protection plug is a more or less elastically deformable ear protector to be inserted in the outer portion of the ear canal by the fingers, thereafter to be held in place by friction and a certain pressure between the plug and the wall of the ear canal.

The classical ear protection plug quite simply is a piece of cotton-wool which is formed by the fingers and is inserted in the ear. Its noise attenuating effect varies with the accuracy with which it has been formed, and the same applies to its capability of being retained in the ear canal. The noise attenuation effect is, at the best, relatively low and the retention capacity depends on the fit and pressure of the cotton-wool plug in the ear canal. The main advantage of an ear protection plug of this type is that the cotton-wool material is cheap and thus well suited for single use. The main drawbacks are its relatively poor noise damping effect, a varying capability of being retained in the ear canal, and a pressure in the ear canal that increases with increasing retention capability, which means greater discomfort to the user.

Departing from such cotton-wool plugs, many different types of ear protection plugs have been developed which have an improved noise attenuating effect and retention capability and which cause less discomfort in the ear, a common feature of all ear protection plugs which have displayed a good noise attenuating effect and a good retention capability without causing discomfort to the ear, being however that they are relatively expensive and therefore are used several times in order to reduce cost per time of use. Repeated use in many cases is a serious hygienic problem. Within many fields, for instance in the armed forces, the engineering industry etc., use is often made of ear protection plugs instead of earmuffs since ear plugs are lighter and less cumbersome to wear. When used for the first time, the plugs can be inserted in the ears without being seriously contaminated by dirty fingers, but if they are used several times and are handled by dirty fingers and between uses are kept on a dirty work-table or drop to the floor, contamination is of course greatly increased and so is the risk of infection in the auditory canals.

The object of the invention is to provide an elastic ear protection plug which has a good noise attenuating and retention capability and which is comfortable to wear or, at least, causes minimum discomfort and which is so cheap that it need not tempt the user to wear it more than once.

As is known, ear canals have elliptic or ovoid cross-section and the dimensions of the section are of different size in different people. Thus, females and children have smaller ear canals than males, the size also varying with the size of the body. Elastic ear protection plugs whose cross-section can be reduced or shaped by the fingers or by pressing the plug into the ear canal, can within certain limits be adapted to ear canals of different size and shape. Thus, in the manufacture of ear plugs, it has been possible to restrict the number of different sizes to a relatively small number of standard sizes, but it would be possible further to lower the costs of manufacture and stock-keeping to a not insignificant extent if the number of standard sizes could be reduced.

Thus, the invention also has for its object to provide an ear protection plug which reduces the number of necessary standard sizes to about the half.

These objects have now been achieved in that the ear protection plug according to the invention has been given the features stated in claim 1 and, in preferred embodiments, the features which are stated in claims 2–9.

A further object of the invention is to provide a method for economical mass production of ear protection plugs according to the invention, this object having been achieved in that the method has been given the features which are stated in claims 10 and 11.

The invention will be described in greater detail hereinbelow with reference to the accompanying drawing, in which FIG. 1 shows an ear protection plug according to the invention in side elevation and partly in section, FIG. 2, in a view similar to that of FIG. 1, shows a modified embodiment of the invention, FIG. 3 is a side elevation of a further modified embodiment of the invention, FIG. 4, in top plan view, shows a mould for the production of ear protection plugs according to the invention, one part of the mould being partially broken away to illustrate the inner side of the other part, and FIG. 5 is a fragmentary section of the mould taken along the line V—V in FIG. 4.

As shown in FIG. 1, the ear protection plug according to the invention comprises a closed gas-filled body of elastic material, preferably plastic, such as PVC plastic or any other suitable plastic which has elastic properties and does not irritate the skin.

The plug in FIG. 1 has a relatively small wall thickness, such as about 0.5–1.3 mm, the preferred range being 0.6–1.1 mm. A thickness of the wall 1 of 0.9 mm has been found extremely suitable for an ear protection plug according to the invention of normal size, i.e. standard size for a large number of people with ear canals of normal size and within a relatively extended range of varying sizes on either side of the normal size.

The ear protection plug preferably has circular cross-section which, however, can be readily formed after the shape of the ear canal by elastic deformation. The longitudinal section is approximately ovoid and, in the preferred embodiment, is more precisely substantially oval at apposite end portions 2, 3 and substantially conical along a central portion 4 interconnecting the end portions.

The two end portions 2, 3 in FIG. 1 may be each of a length of 10 mm, while the substantially or approximately conical central portion 4 is of a slightly shorter length, such as 7–8 mm. In FIG. 1, the lengths of the three portions 2–4 are indicated on the axis of the ear protection plug and are designated A, B, C, the length of the central portion 4 being designated B. The diameter between sections A and B in the illustrated embodiment is 8 mm and the diameter between sections B and C is 10 mm.

These measures are the preferred ones for the above standard size which fits many people having an ear canal of average size and within an extended range on either side thereof. Apart from this standard size, only one or a few larger standard sizes are required for people having ear canals of sizes outside the range just stated and a few smaller standard sizes. For larger or smaller sizes the cross-sectional diameters are increased or decreased, respectively, but it is not absolutely necessary to perform a corresponding proportional modification of the indicated measures of length.

The shape of the ear protection plug according to the invention should rather be defined as ovoid, it being possible for people having smaller ear canals within the range of size for which the plug is intended, to use the plug by inserting it in the ear with the narrow end portion first, while people having larger ear canals can use the plug by inserting it in the ear with the thick end portion first. Since the plug can be reversed and has two end portions of different size, the number of required standard sizes can be reduced by half as compared with ear protection plugs with only one usable end portion or two similar usable end portions.

The ear protection plug shown in FIG. 2 corresponds as regards the stated dimensions to the plug of FIG. 1 but has at opposite end portions cavity-forming wall incurvations 5, 6 which may be substantially cylindrical or slightly conical circumferential walls, preferably with cup-shaped bottoms. The length of the incurvations may be about 5 mm for both end portions but the diameter of the incurvation at the thick end preferably is slightly larger than the diameter of the incurvation at the narrow end. At the thick end, the diameter of the incurvation preferably is 5 mm and at the narrow end 4 mm. The purpose of these incurvations is the same as that of the cavity in the front end portion of the ear protection plug disclosed in Swedish printed application No. 7411263-2, i.e., after insertion of the plug, to create a slight depression in the ear canal in that the boundary wall of the cavity after deformation of the plug tends to resume its natural shape and thus to expand again after the deformation.

The ear protection plug shown in FIG. 3 has a narrow end portion 2', a thick end portion 3' and a central portion 4' interconnecting portions 2' and 3'. These portions differ from the corresponding portions of the plug in FIG. 1 in that the differences between the diameters of the end portions are greater than in the embodiment of FIG. 1. Between the substantially conical central portion 4' and the thick end portion 3' there is thus provided a shoulder with a rounded concave transition at 7'. The ear protection plug in FIG. 3 can be used for ear canals within a larger range of size as compared with the plug of FIGS. 1 and 2.

The elastically deformable gas-filled ear protection plug according to the invention can be deformed by the fingers prior to insertion in the ear. By finger pressure the diameter can be reduced, causing extension of the plug, and it is of course possible to flatten the plug by finger pressure. After insertion in the ear canal, the plug tends to resume its natural shape, i.e. it tends again to expand and thus adapts to the shape of the ear canal, and by its excellent adaptation to the shape of the ear and its urge to expand, both satisfactory fit and suitable retention force in the ear canal are gained. The noise attenuating effect of the plug is most satisfactory in that the wall volume is small in relation to the total volume.

In the embodiment shown in FIGS. 1 and 2, the closed cavity 10 of the plug is completely empty (apart from the gas), but it is possible to manufacture an ear protection plug according to the invention in such a manner that the interior of the plug is formed of a cellular structure in that the plug is made of foaming plastic which has a smooth outer surface.

Ear protection plugs according to the invention can be mass-produced by means of a mould of the type shown in FIGS. 4 and 5 and in the manner described below.

The mould in FIG. 4 consists of two parts 11, 12 which may be of rectangular or square section. Each mould part 11, 12 has a number of cells 13 and 14, respectively, (see FIG. 5) open at the inner side of each mould part. The parting line between the mould parts 11, 12 corresponds to the plane where the ear protection plug in FIG. 1 has its largest diameter, i.e. between sections B and C.

The mould walls between the cells 13, 14 of the two mould parts 11, 12 can be relatively thin. Thus, a square or rectangular shape as shown in FIG. 4 with an area of for instance 1 $m^2$ will hold about 2000 moulding cells 13, 14.

The production is carried out in such a way that one mould part, for instance the lower mould part 12 in FIG. 5, is immersed in a bath containing liquid thermoplastic material. The two mould parts 11, 12 are then closed. The closed mould is rotated by means of a suitable device according to the centrifugal or rather rotational moulding or casting method for a sufficient time and at a suitable temperature in order to cause the plastic material to set. For PVC plastic, it is sufficient to rotate the mould at such a low speed as about 8-12 r.p.m. for a time as short as about 4 min at a temperature of 190° C. However, r.p.m., time and temperature depend on the plastic used for moulding.

For the manufacture of plugs of cellular plastic, use is made of a plastic material with an admixture of a foaming or blowing agent.

The advantage of the production method according to the invention is that it permits a very cheap large-scale production with relatively simple aids. The advantages of the protection plugs according to the invention will be apparent from the drawbacks that are eliminated. Thus, there will be no high expanding pressure from the plug in the ear canal and the user can himself adjust the pressure depending on how far the plug is inserted in the ear. The noise attenuation effect is very good owing to a small mass volume in relation to the total volume and very good adaptation against the wall of the ear canal. Inflamed ears is a common consequence of the use of plugs dirty from handling. This may be avoided in that the ear protection plugs of the invention are so cheap that no one need hesitate to dispose of a pair of ear protection plugs used once. As an example of the importance of economizing it may be mentioned that the cost of conventional ear protection plugs for the personnel in a medium-size weaving mill amounts to about Sw.kr. 800–1000 per person and year. This cost can be substantially reduced by the present invention.

The invention is not restricted to the embodiments described above but may be modified in various ways within the spirit and scope of the accompanying claims.

I claim:

1. An ear protection plug of elastic material, characterized in that the ear protection plug is in the form of a closed gas-filled body with an elastic wall (1) and of approximately ovoid longitudinal section, so as to have a first relatively thick end portion (3) and an opposite relatively narrow second end portion (2), each of said end portions having a decreasing cross-sectional diameter in the direction towards the respective end, such that the plug has two opposite insertion ends and permits optionally inserting the ear protection plug either with the thick or with the narrow insertion end in the ear canal to fit ear canals of varying size and/or shape.

2. Plug as claimed in claim 1, characterized in that the two end portions (2, 3) are interconnected by a central portion (4) of substantially or approximately conical shape.

3. Plug as claimed in claim 1 or 2, characterized in that it has a wall thickness of between 0.5 and 1.4 mm and preferably 0.7–1.1 mm.

4. Plug as claimed in claims 1 or 2, characterized in that it is made of PVC plastic as a continuous piece by centrifugal casting.

5. Plug as claimed in claim 1 or 2, characterized in that it is made as a continuous piece by centrifugal casting and has a closed gas-filled cavity defined by the wall (1) of the plug.

6. Plug as claimed in claim 1 or 2, characterized in that it is made as a continuous piece by centrifugal casting of foaming plastic.

7. Plug as claimed in claims 1 or 2, characterized in that the plug in each end has a cavity open towards the end of the plug and provided by an incurvation in the plug wall at each end of the plug.

8. Plug as claimed in claim 7, characterized in that the cavity has a depth of about 5 mm and a diameter of about 4–5 mm.

9. Plug as claimed in claims 1 or 2, characterized in that said central portion (4) merges into the thick end portion (3) of the plug from a smaller to the largest diameter of the thick end portion (3) by a shoulder of preferably concavely rounded or conical shape.

* * * * *